(12) United States Patent
Otsubo

(10) Patent No.: US 7,763,002 B2
(45) Date of Patent: Jul. 27, 2010

(54) DISPOSABLE PULL-ON TYPE DIAPER

(75) Inventor: Toshifumi Otsubo, Kagawa-ken (JP)

(73) Assignee: Uni-Charm Corporation (JP)

( * ) Notice: Subject to any disclaimer, the term of this patent is extended or adjusted under 35 U.S.C. 154(b) by 47 days.

(21) Appl. No.: 11/695,188

(22) Filed: Apr. 2, 2007

(65) Prior Publication Data
US 2007/0239129 A1 Oct. 11, 2007

(30) Foreign Application Priority Data
Apr. 6, 2006 (JP) .............................. 2006-105663
Nov. 14, 2006 (JP) .............................. 2006-308358

(51) Int. Cl.
*A61F 13/15* (2006.01)

(52) U.S. Cl. .......................... 604/385.101; 604/385.01; 604/385.28

(58) Field of Classification Search ............ 604/385.01, 604/385.101, 385.24–385.28
See application file for complete search history.

(56) References Cited

U.S. PATENT DOCUMENTS 5,554,145 A * 9/1996 Roe et al. ................ 604/385.3
5,653,842 A 8/1997 Kuen
6,786,895 B1 * 9/2004 Schmitz ................. 604/385.28
7,033,341 B2 * 4/2006 Mishima ................ 604/385.01
2004/0039363 A1 * 2/2004 Sugiyama et al. ..... 604/385.101
2004/0193134 A1 * 9/2004 Mueller et al. ........ 604/385.101
2005/0038401 A1 2/2005 Suzuki et al.
2005/0273073 A1 12/2005 Suzuki et al.

FOREIGN PATENT DOCUMENTS

| JP | 08-322878 | 12/1996 |
|---|---|---|
| JP | 2000-296148 | 10/2000 |
| JP | 2002-011044 | 1/2002 |

* cited by examiner

*Primary Examiner*—Tatyana Zalukaeva
*Assistant Examiner*—Lynne Anderson
(74) *Attorney, Agent, or Firm*—Lowe Hauptman Ham & Berner, LLP

(57) ABSTRACT

A disposable pull-on type diaper has a separator interposed between an inner surface of an absorbent chassis and the wearer's skin so as to protect the diaper wearer's skin from being soiled with feces. The separator is formed by a piece of sheet extending from a bottom of a crotch region of the diaper toward a front waist region and a rear waist region and fixed to lateral edges of the crotch region. The piece of sheet has a front end and a rear end both extending in a transverse direction of the crotch region. These front end and rear end are free along middle segments thereof as viewed in the transverse direction of the crotch region from an inner surface of an absorbent chassis and inseparably integrated with each other.

17 Claims, 15 Drawing Sheets

DISPOSABLE PULL-ON TYPE DIAPER

BACKGROUND OF THE INVENTION

The present invention relates to a disposable pull-on type diaper and particularly to a pull-on type diaper devised to protect the wearer's skin from being contaminated with feces.

The disposable diaper devised to prevent feces from coming in contact with and contaminating the user's skin is well known. For example, the pull-on type diaper disclosed in Japanese Unexamined Patent Application Publication No. 2002-11044 (hereinafter referred to as "REFERENCE") is provided on the topsheet with the skin contact sheet on and this skin contact sheet is formed in the crotch region with the opening around which elastic member is attached in a stretched state to the skin contact sheet. This opening may be adjusted to fall in with the user's anus to ensure that discharged feces is reliably led through the opening into a space defined under the skin contact sheet and prevented from coming in contact with the user's skin.

In the case of the diaper disclosed in REFERENCE, should the opening formed through the skin contact sheet is out of correctly falling in with the user's anus, there will be a possibility that feces might flow into a space defined between the user's skin and the skin contact sheet and unacceptably contaminate the user's skin. In other words, for this known diaper, it is essential to make the opening of the skin contact sheet correctly fall in with the user's anus. However, it is impossible for mother or helper to determine whether the opening falls in with the user's anus or not from the outside. Certainly, the skin contact sheet is provided with a notch to assure that urine passing through this notch is directly absorbed by the absorbent core. However, it can not be avoided that urine passed through the notch is mixed with feces on the surface of the absorbent core. Once mixed with urine, feces becomes loose and consequentially a possibility that the user's skin might be contaminated with such loose feces.

SUMMARY OF THE INVENTION

In view of the problem unsolved behind by the prior art as has been described above, it is one of the objects of the present invention to provide a novel diaper adapted to facilitate a feces receiving space of the diaper to be adjusted to fall in with the wearer's anus.

It is another object of the invention to provide a novel diaper adapted to prevent urine and feces from being mixed together.

It is still another object of the invention to provide a novel diaper adapted to prevent leak of body fluids from occurring around the wearer's legs.

According to the present invention, there is provided a disposable pull-on type diaper having a crotch region, a front waist region extending forward from the crotch region and a rear waist region extending rearward from the crotch region wherein the front waist region and the rear waist region are joined together along respective lateral edges thereof so as to a pull-on type diaper chassis which is, in turn, provided on its inner surface with a separator serving to protect the wearer's skin from coming in contact with feces discharged by the wearer.

The present invention further comprises aspects as will be described. The separator comprises a piece of sheet extending in a longitudinal direction from a center of the crotch region toward the front waist region as well as toward the rear waist region, and extending so as to stride across a longitudinal center line bisecting a width of the crotch region and to be fixed to the inner surface of the absorbent chassis on both sides of the longitudinal center line. The sheet has a front end extending in the transverse direction across the crotch region in a zone thereof set aside toward the front waist region or across the front waist region and a rear end extending in the transverse direction across the crotch region in a zone thereof set aside toward the rear waist region or across the rear waist region and wherein both the front end and the rear end are inseparably integrated with each other on the longitudinal center line and respectively have intermediate segments in the transverse direction free from the inner surface of the diaper chassis.

According to one preferred embodiment of the invention, the crotch region has lateral edges extending in the longitudinal direction of the pull-on type diaper, the lateral edges respectively defining leg-holes and being provided with leg-encircling elastic members attached in a stretched state thereto so as to define leg-encircling elastic zones adapted to be stretchable/contractible in a circumferential direction around each of the leg-holes and the front end as well as the rear end of the separator extend to the lateral edges and are joined to the inner surface of the absorbent chassis in the leg-encircling elastic zones.

According to another preferred embodiment of the invention, the crotch region has lateral edges extending in the longitudinal direction of the pull-on type diaper, the lateral edges respectively defining leg-holes and being provided with leg-encircling elastic members attached in a stretched state thereto so as to define leg-encircling elastic zones adapted to be stretchable/contractible in a circumferential direction around each of the leg-holes and the front end as well as the rear end of the separator extend to the lateral edges and are joined to the inner surface of the absorbent chassis at points set aside from the leg-encircling elastic zones toward the longitudinal center line.

According to still another preferred embodiment of the invention, the front end and the rear end of the separator include a front elastic zone and a rear elastic zone, respectively, both adapted to be stretchable/contractible in the transverse direction of the crotch region.

According to yet another preferred embodiment of the invention, the separator is joined to an inner surface of a bottom of the crotch region along a joining line extending in the transverse direction of the diaper so as to bisect the separator in the longitudinal direction of the diaper.

According to further another preferred embodiment of the invention, the piece of sheet forming the separator comprises a front piece of sheet lying in the crotch region aside toward the front waist region and a rear piece of sheet separately provided and lying in the crotch region aside toward the rear waist region so that the front piece of sheet has the front end and the rear piece of sheet has the rear end.

According to one alternative preferred embodiment of the invention, the front piece of sheet has a front bottom end extending in parallel to the front end at the bottom of the crotch region while the rear piece of sheet has a rear bottom end extending in parallel to the rear end at the bottom of the crotch region and the front bottom end as well as the rear bottom end is joined to the inner surface of the bottom of the crotch region along joining lines extending in the transverse direction of the crotch region.

According to another alternative preferred embodiment of the invention, the crotch region comprises, in a middle zone in the transverse direction, a body fluid absorbent core containing at least one of fluff pulp and super-absorbent polymer particles and, on both sides of the absorbent core, flaps each containing at least one of nonwoven fabrics and plastic films and having a flexural stiffness lower than that of the absorbent core and wherein the leg-encircling elastic zones are formed in the flaps, respectively.

According to still another alternative preferred embodiment of the invention, the front waist region and the rear waist region are joined together in a detachable and reattachable manner so that the front and rear waist regions may be joined together to take a pull-on type immediately before the diaper is put on a wearer's body.

The disposable pull-on type diaper according to the present invention has the separator serving to prevent feces and urine from being mixed together. The separator has lateral edges fixed to the inner surface of the diaper on both sides of the longitudinal center line and has the front end and the rear end. These front and rear ends are inseparably integrated with each other on the longitudinal center line and respectively have intermediate segments free from the inner surface of the absorbent chassis in a middle zone of the crotch region as viewed in the transverse direction. When the front and rear waist regions are spaced from each other in the back-and-forth direction and thereby the waist-hole is broadened in order to put the diaper on the wearer's body, the front and rear ends lying on the right side with respect to the longitudinal center line are also spaced from each other in the back-and-forth direction so that the right leg of the wearer can be led through the space defined between these ends. Similarly, the front and rear ends lying on the left side with respect to the longitudinal center line are also spaced from each other in the back-and-forth direction so that the left leg of the wearer can be led through the space defined between these ends. The opening is formed between the front end of the separator and the inner surface of the absorbent chassis so that urine can be led through this opening and the other opening is formed between the rear end of the separator and the absorbent chassis so that feces can be led through this opening. In this manner, urine and feces flow through the space defined between the separator and the inner surface of the absorbent chassis and therefore it is not apprehended that the wearer's skin might be soiled with such urine and/or feces. In addition, the separator serves also at the bottom of the crotch region as the partition functioning to prevent urine and feces from being mixed together.

With the embodiment in which the lateral edges of the crotch region respectively include stretchable/contractible leg-encircling elastic zones and the front end as well as the rear end of the separator is joined to the inner surface of the diaper chassis in these leg-encircling elastic zones, the front end and the rear end of the separator pull the lateral edges of the crotch region toward the longitudinal center line so as to raise these lateral edges with respect to the inner surface of the diaper and thereby to form leak-barriers along the lateral edges of the diaper.

With the embodiment in which the front end and the rear end of the separator respectively include the front elastic zone and the rear elastic zone both being stretchable/contractible in the transverse direction of the crotch region, the separator can be held in close contact with the inner sides of the wearer's legs and thereby prevent leak of body fluids from occurring around the wearer's legs.

With the embodiment in which the separator is joined to the inner surface of the bottom of the crotch region along the joining line extending in the transverse direction of the crotch region, it can be reliably prevented that urine and feces led into the space defined between the separator and the inner surface of the diaper might be mixed together.

The other embodiments of the present invention and advantages obtained by these embodiments will be understood from the description given hereunder more in details.

DETAILED DESCRIPTION OF THE PREFERRED EMBODIMENTS

Details of a disposable pull-on type diaper according to the present invention will be more fully understood from the description given hereunder with reference to the accompanying drawings.

Figure 1:
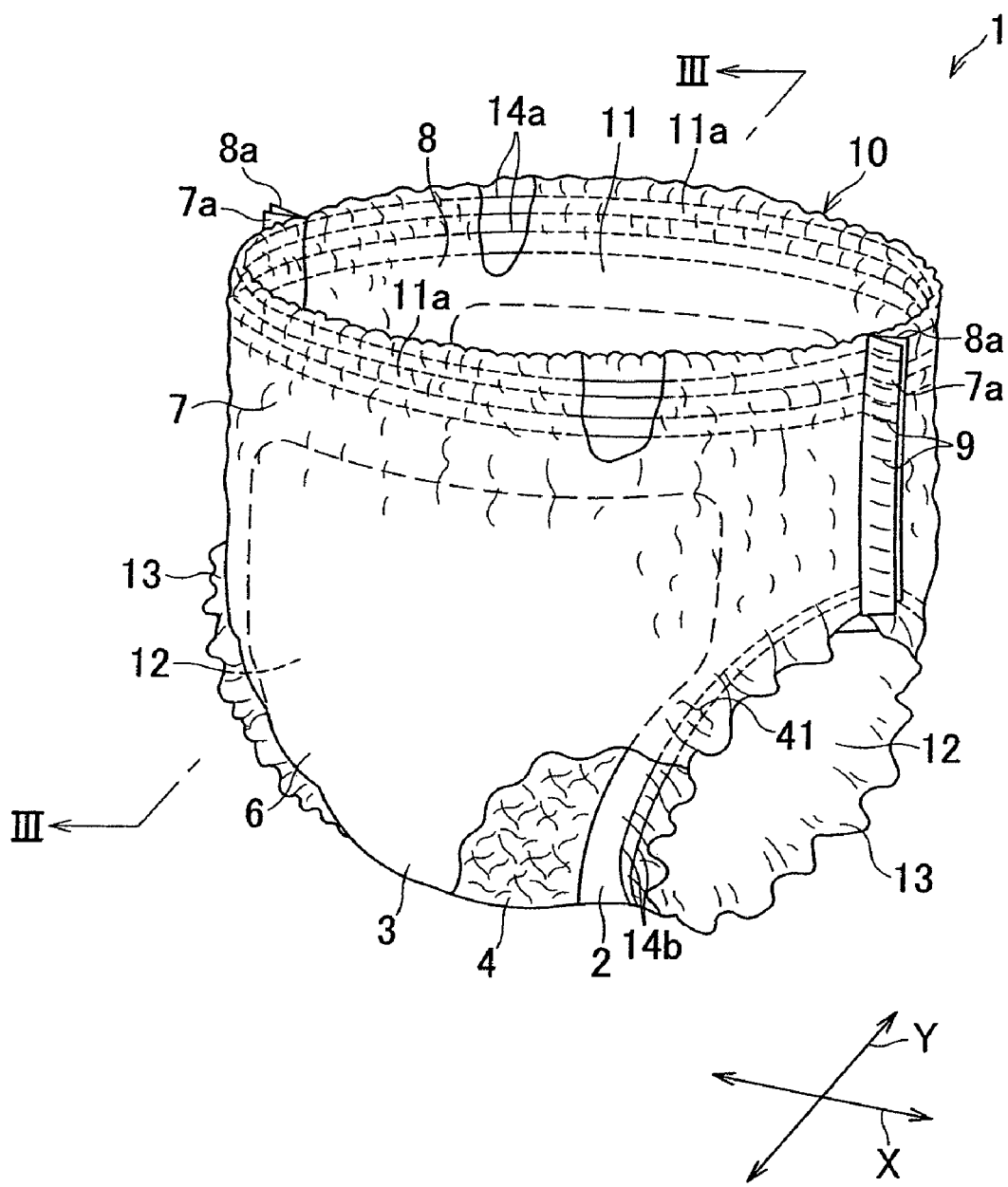
FIG. 1 is a perspective view, partially cutaway, showing a pull-on type diaper.

FIG. 1 is a partially cutaway perspective view showing a pull-on type diaper 1 according to the invention in a state put on a wearer's body. The pull-on type diaper 1 has a pull-on type absorbent chassis 10 comprising a liquid-pervious inner sheet 2, a liquid-impervious outer sheet 3 and a body fluid absorbent core 4 sandwiched between these two sheets 2, 3. The absorbent chassis 10 comprises a crotch region 6, a front waist region 7 extending forward from the crotch region 6 and a rear waist region 8 extending rearward from the crotch region 6. The front and rear waist regions 7, 8 respectively have lateral edges 7a, 8a put flat together and welded together at joint spots 9 arranged intermittently in the vertical direction as viewed in FIG. 1 so as to form a waist-hole 11 and a pair of let-holes 12. In the vicinity of the waist-hole 11, a plurality of waist-encircling elastic members 14a circumferentially extending around the waist are sandwiched between the inner and outer sheets 2, 3 and bonded in a stretched state to at least one of these inner and outer sheets 2, 3. In the vicinity of peripheries 13 of the respective leg-holes 12, a plurality of leg-encircling elastic members 14b circumferentially extending around respective legs are sandwiched between the inner and outer sheets 2, 3 and bonded in a stretched state to at least one of these inner and outer sheets 2, 3 so as to form annular elastic regions extending around the respective legs.

Figure 2:
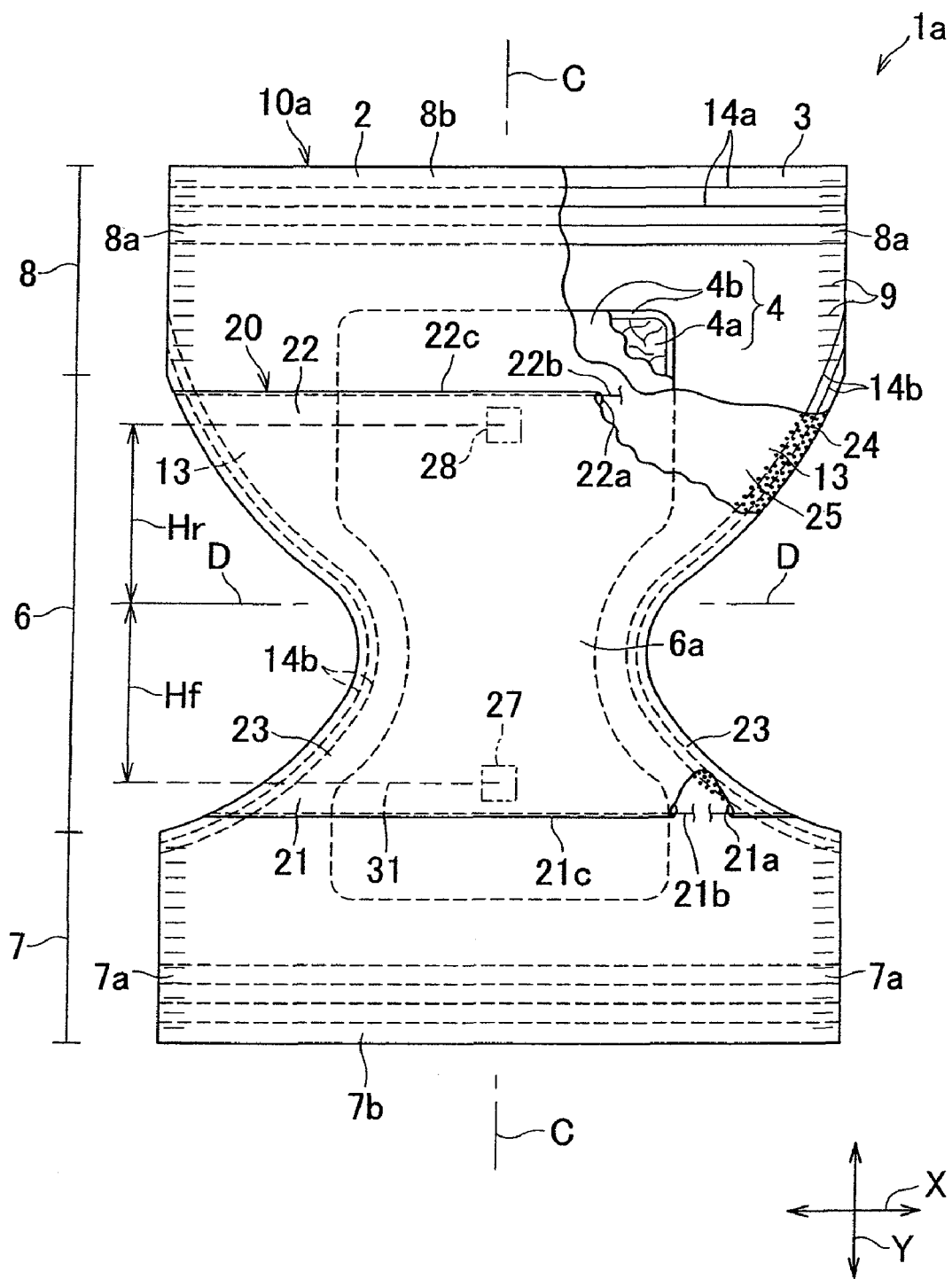
FIG. 2 is a plan view showing the pull-on type diaper with front and rear waist regions disconnected from each other and developed.

FIG. 2 is a partially cutaway plan view of the developed diaper 1a obtained by peeling the front and rear waist regions 7, 8 of the pull-on type diaper 1 shown in FIG. 1 off from each other at the joint spots 9 and then developing the pull-on type diaper 1 in a transverse direction indicated by a double-headed arrow X as well as in a longitudinal direction indicated by a double-headed arrow Y which is orthogonal to the direction X. It will be understood that the inner surface faces of this developed diaper 1a faces the viewer of this FIG. 2. As viewed in FIG. 2, the absorbent chassis 10 is generally hourglass-shaped and the periphery of the waist-hole 11 shown in FIG. 1 appears herein as a front end 7b and a rear end 8b while the peripheries 13 of the respective leg-holes 12 appear herein as lateral edges 13 of the crotch region 6. While the lateral edges 13 respectively bow toward a longitudinal center line C-C bisecting a width of the crotch region 6 in the developed diaper 1a, the lateral edges 7a, 8a of the front and rear waist regions 7, 8 being contiguous to the respective lateral edges 13 extend in the longitudinal direction Y in parallel to the center line C-C. The core 4 also is generally hourglass-shaped and comprises a mixture 4a of fluff pulp and super-absorbent polymer particles wrapped with a covering sheet 4b such as tissue paper permitting body fluids to be efficiently absorbed and spread in high absorbency and spread. The inner sheet 2 defining the inner surface of the absorbent chassis 10 is provided in the crotch region 6 with a separator 20 formed from hydrophobic sheet materials, preferably hydrophobic and liquid-impervious sheet materials. The separator 20 has lateral edges 23 fixed to the lateral edges 13 of the crotch region 6, respectively, by hot melt adhesives 24, a front end 21 lying in the crotch region 6 aside toward the front waist region 7 so as to extend in the transverse direction X to the respective lateral edges 13 and a rear end 22 lying in the crotch region 6 aside toward the rear waist region 8 so as to extend in the transverse direction X to the respective lateral edges 13. Large extent of the separator 20 except the lateral edges 23 is free from the inner sheet 2. Along the front and rear ends 21, 22, sleeves 21a, 22a are formed by folding back the separator 20. These sleeves 21a, 22a contain therein front and rear elastic members 21b, 22b, respectively, which are bonded in a stretched state to respective inner sides of these sleeves 21a, 22a so as to define front and rear elastic zones, respectively, extending between the lateral edges 13. On the respective lateral edges 13, these elastic zones intersect with elastic zones defined by the respective leg-encircling elastic members 14b. The front end 21 and the rear end 22 are respectively spaced from a transverse center line D-D bisecting a dimension of the absorbent chassis 10 in the longitudinal direction Y by distances Hf, Hr, respectively, which are generally equal to each other. The separator 20 is provided in the vicinity of these ends 21, 22 with a front joint zone 27 and rear joint zone 28 both lying on the longitudinal center line C-C as indicated by imaginary lines. When the developed diaper 1a is folded inward along the center line D-D on itself, the front joint zone 27 and the rear joint zone 28 fall in with each other and are bonded together to form a joint 35 (See FIG. 3). The core 4 sandwiched between the inner sheet 2 and the outer sheet 3 extends across the crotch region 6 in the longitudinal direction Y preferably beyond the front end 21 and the rear end 22 as illustrated. The separator 20 of such an arrangement cooperates with the inner sheet 2 from which the separator 20 is free to form a tunnel- or pocket-like space 31 adapted to receive bodily discharges.

Figure 3:
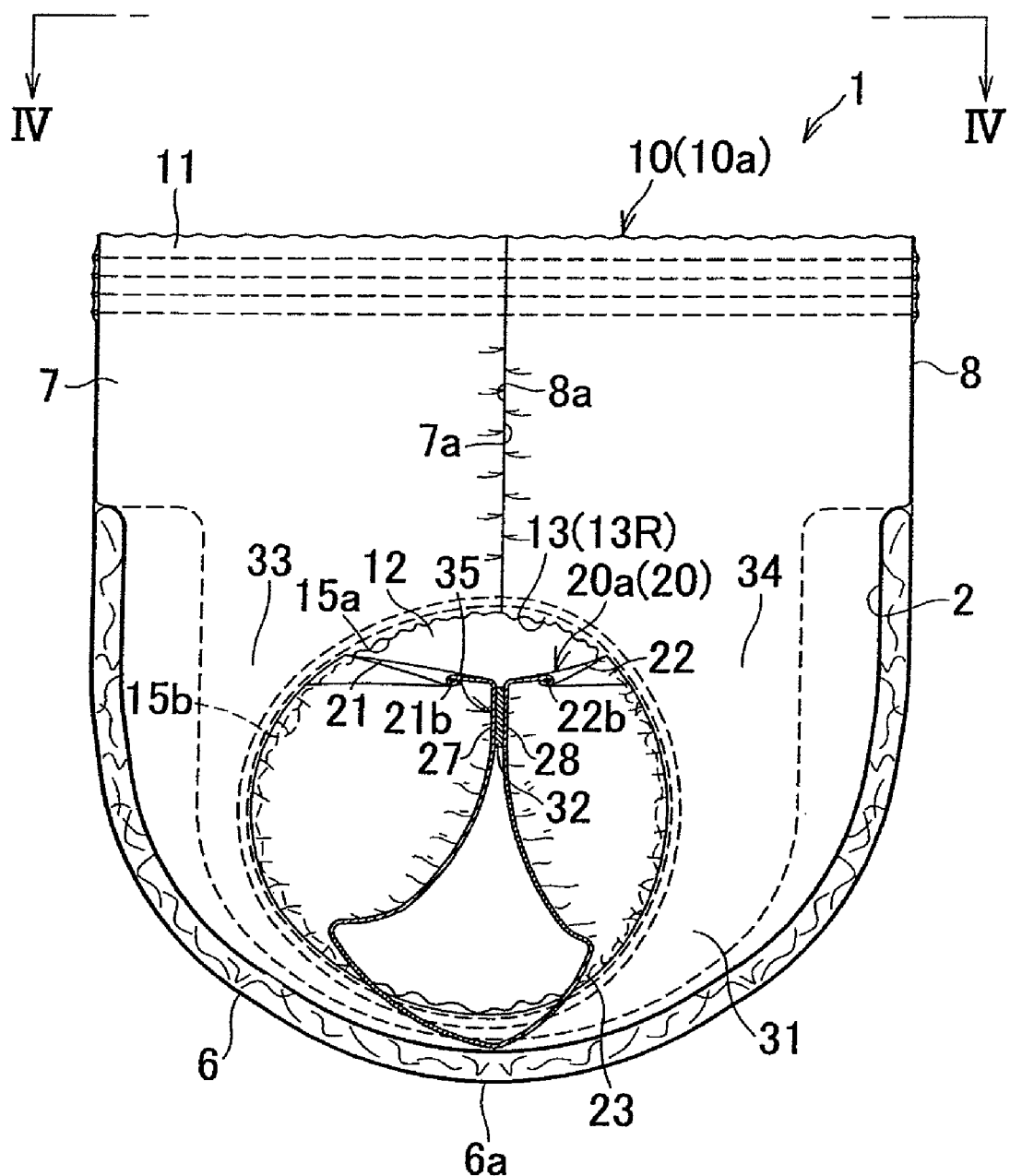
FIG. 3 is a sectional view taken along the line III-III in FIG. 1.

FIG. 3 is a sectional view taken along the line III-III in FIG. 1 which falls upon the longitudinal center line C-C in FIG. 2. Of the absorbent chassis 10, the front and rear waist regions 7, 8 are joined together along the respective lateral edges 7a, 8a and the crotch region 6 bows in a U-shape and the lateral edges 13 thereof respectively define the leg-holes 12. Of the separator 20, the front and rear ends 21, 22 are permanently bonded in the front and rear joint zones 27, 28, respectively, by hot melt adhesives 32 or sealing technique to define the joint 35. The bodily discharge receiving space 31 formed between the separator 20 and the inner sheet 2 has a front opening 33 defined by the front end 21 and the inner sheet 2 and a rear opening 34 defined by the rear end 22 and the inner sheet 2. At a bottom 6a of the crotch region 6, the inner sheet 2 and the separator 20 are substantially or actually in contact with each other.

Figure 4:
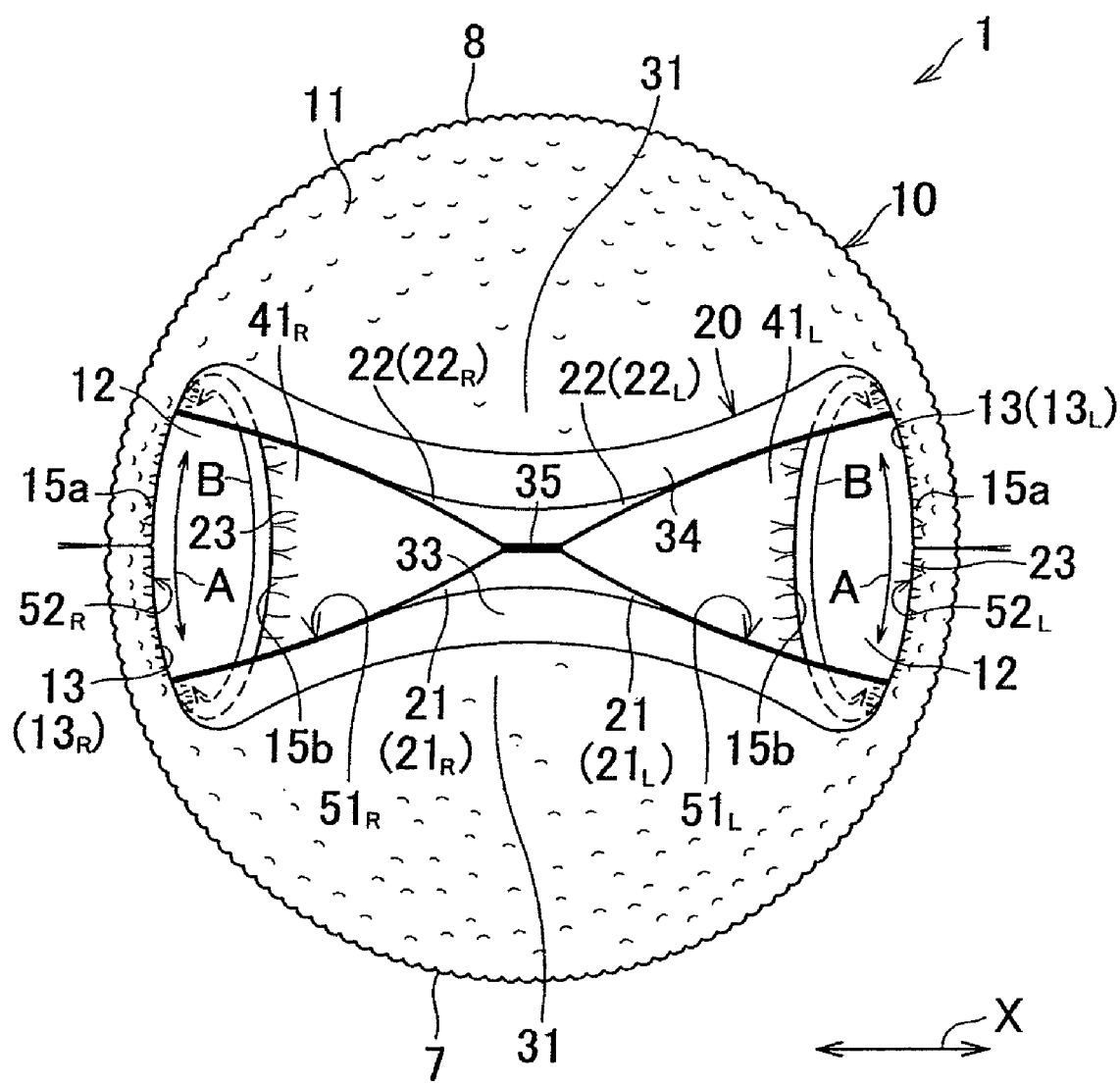
FIG. 4 is a sectional view taken along the line IV-IV in FIG. 3.

FIG. 4 is a sectional view taken along the line IV-IV in FIG. 3, showing the diaper 1 of FIG. 1 as viewed from above the waist-hole 11. The front end 21 of the separator 20 has its dimension in the transverse direction X bisected by the joint 35. Thus the front end 21 comprises a right front end $21_R$ adapted to be held in close contact with the right leg of the wearer (not shown) and a left front end $21_L$ adapted to be held in close contact with the wearer's left leg. These right and left front ends $21_R$, $21_L$ describe together a V-shape. Similarly, the rear end 22 has its dimension in the transverse direction X bisected by the joint 35. The rear end 22 thus comprises a right rear end $22_R$ adapted to be held in close contact with the wearer's right leg and a left rear end $22_L$ adapted to be held in close contact with the wearer's left leg. These ends $22_R$, $22_L$ also describe together a V-shape. In the absorbent chassis 10, the peripheries 13 of the respective leg-holes 12 are designated as a right leg periphery $13_R$ and a left leg periphery $13_L$ in FIG. 4. Each of these peripheries $13_R$, $13_L$ comprises an upper periphery 15a free from the associated lateral edge 23 and a lower periphery 15b bonded to the associated lateral edge 23 (See FIG. 3 also). Referring to FIG. 4, these upper and lower peripheries 15a, 15b are indicated by double-headed arrows A and B, respectively.

Now the sequence for wearing such pull-on type diaper 1 will be described together with the behavior of the pull-on type diaper 1 will be described. The sequence starts with setting the front and rear waist regions 7, 8 apart from each other in a back-and-forth direction Y to broaden the waist-hole 11 as seen in FIGS. 1 and 4. Thereupon the front end 21 of the separator 20 is deformed into the V-shape, i.e., the right front end $21_R$ and the left front end $21_L$ form an angle with each other about the joint 35. Similarly, the right rear end $22_R$ and the left rear end $22_L$ form an angle with each other and thereby the rear end 22 is deformed into the V-shape. Such deformation causes the front opening 33 and the rear opening 34 to be automatically broadened (See FIG. 3). Simultaneously, the right front end $21_R$ and the right rear end $22_R$ are significantly spaced from each other while the left front end $21_L$ and the left rear end $22_L$ are significantly spaced from each other. Then the right leg of the wearer (not shown) is led through the right leg-opening $41_R$ defined by the upper periphery 15a of the right leg encircling periphery $13_R$ for the right leg-hole 12, the right front end $21_R$ of the separator 20 and the right rear end $22_R$. Without interruption, the right leg is led through the right leg-hole 12 defined by the upper and lower peripheries 15a, 15b of the right leg encircling periphery $13_R$. Then, the left leg is led through the left leg-opening $41_L$ defined by the upper periphery 15a of the left leg encircling periphery $13_L$, the left front end $21_L$ and the left rear end $22_L$. Without interruption, the left leg is led through the left leg-hole 12 defined by the upper and lower peripheries 15a, 15b of the left leg encircling periphery $13_L$. With the pull-on type diaper 1 put on the wearer's body in the manner as has been described above, the peripheries 13 of the respective leg-holes 12, i.e., the right leg periphery $13_R$ and the left leg periphery $13_L$ are elastically stretchable/contractible in the circumferential direction of the respective holes 12 while the front and rear ends 21, 22 of the separator 20 are elastically stretchable/contractible in the transverse direction X. Consequentially, the upper periphery 15a, the right front end $21_R$ and the right rear end $22_R$ are elastically held in close contact with the wearer's right leg in the vicinity of the inguinal region so as to form a primary seal $51_R$ serving to prevent leak of bodily fluids from occurring around the wearer's right leg. Below the primary seal $51_R$, the lower periphery 15b cooperates with the upper periphery 15a to form a secondary seal $52_R$ serving to prevent leak of bodily fluids from occurring around the wearer's right leg. This secondary seal $52_R$ serves in the same manner as the seal assured around the wearer's leg in the pull-on type diaper of prior art. With respect to the left leg also, the upper periphery 15a, the left front end $21_L$ and the left rear end $22_L$ are elastically held in close contact with the wearer's left leg in the vicinity of the inguinal region so as to form a primary seal $51_L$ serving to prevent leak of bodily fluids from occurring around the wearer's left leg. Below the primary seal $51_L$, the lower periphery 15b cooperates with the upper periphery 15a to form a secondary seal $52_L$ serving to prevent leak of bodily fluids from occurring around the wearer's left leg. The pull-on type diaper 1 put on the wearer's body in this manner may be further pulled up along the wearer's body to ensure that, in the vicinity of the joint 35, the front and rear ends 21, 22 of the separator 20 come in contact with the wearer's crotch region between the external genital and the anus. The pull-on type diaper 1 put on the wearer's body still maintains the front and rear ends 21, 22 of the separator 20 spaced apart from the inner sheet 2 and the front and rear openings 33, 34 sufficiently broadened.

In the pull-on type diaper 1 put on the wearer's body in this manner, the separator 20 clearly partitions the diaper wearer's crotch region into a front half and a rear half so that the wearer's external genital faces the front opening formed in this front half and the anus faces the rear opening formed in the rear half. Consequentially, it is ensured that urine discharged from the external genital is guided through the front opening 33 into the bodily discharge receiving space 31 while feces discharged from the anus is guided through the rear opening 34 into the bodily discharge receiving space 31. In this way, the wearer's skin is reliably protected from direct contact with urine as well as with feces. Urine and feces received in the space 31 in this manner are substantially prevented from being mixed together since the inner sheet 2 and the separator 20 are maintained to be closest to each other or to be close contact with each other at the bottom 6a of the crotch region 6. Therefore, there is no anxiety that urine might be mixed with feces so as to increase fluidity of feces and the wearer's skin might be soiled with such feces having high fluidity. Even when urine or feces flows along the legs instead of flowing into the bodily discharge receiving space 31, it is unlikely that bodily discharges might readily leak from the pull-on type diaper 1 because the primary seals $51_R$, $51_L$ and the secondary seals $52_R$, $52_L$ are formed around the respective legs.

Of the pull-on type diaper 1, as stock materials for the inner sheet 2, liquid-pervious nonwoven fabrics, perforated plastic films or the like may be used. Stock materials for the outer sheet 3, liquid-impervious plastic films, nonwoven fabrics of a laminated sheet consisting of such plastic films and non-woven fabrics, or the like may be used. As liquid-absorbent materials for the core 4, fluff pulp, or a mixture of such fluff pulp and super-absorbent polymer particles, or a mixture of such fluff pulp and super-absorbent polymer fibers. As the wrap sheet 4b, nonwoven fabrics may be used in the place of tissue paper. As the sheet material for the separator 20, hydrophobic, or preferably not only hydrophobic but also liquid-impervious nonwovens or plastic films may be used. Preferably, such sheet materials should be elastically or inelastically stretchable as the elastic members 21b, 22b are elastically stretched.

Features of the developed diaper 1a of FIG. 2 will be additionally described. The distance Hf from the transverse center line D-D to the front joint zone 27 is equal to the distance Hr from the transverse center line D-D to the rear joint zone 28. In the case of the preferred separator 20 in the pull-on type diaper 1 for baby, the distances Hf, Hr are in a range of 20 to 150 mm, more preferably in a range of 40 to 80 mm. In the preferred separator 20, a dimension of the joint zone 35 in the transverse direction X is in a range of 3 to 50 mm, more preferably in a range of 10 to 30 mm.

In the developed diaper 1a shown in FIG. 2, the inner and outer sheets 2, 3 extend in the transverse direction X beyond the lateral edges of the core 4 to form a pair of side flaps 25. The side flaps 25 have a flexural stiffness lower than that of the core 4 and respectively define easily deformable portions including elastic zones formed from the inner and outer sheets 2, 3 and the leg-encircling elastic members 14b. When the pull-on type diaper 1 obtained from the developed diaper 1a is in the state as shown in FIG. 1 with the crotch region 6 bowing in the longitudinal direction Y, the side flaps 25 tend to rise up around the respective lateral edges of the core 4 in the vicinity of the transverse center line D-D, i.e., at the bottom 6a of the crotch region 6 as the leg-encircling elastic zones contract. Meanwhile, the lateral edges 23 of the separator 20 are bonded to the inner surface of the leg-encircling elastic zones by adhesives 24 so that the front and rear ends 21, 22 of the separator 20 linearly extending in FIG. 2 are deformed so as to describe the V-shape as seen in FIG. 4. In response to such deformation, the side flaps 25 are pulled by these front and rear ends 21, 22 inward of the pull-on type diaper 1, i.e., toward the longitudinal center line C-C. As a result, the side flaps 25 are further biased to rise up. In this manner, the side flaps 25 are reliably held in close contact with the wearer's legs from below the pull-on type diaper 1 and prevent leak of bodily fluids from occurring around the wearer's legs.

Figure 5:
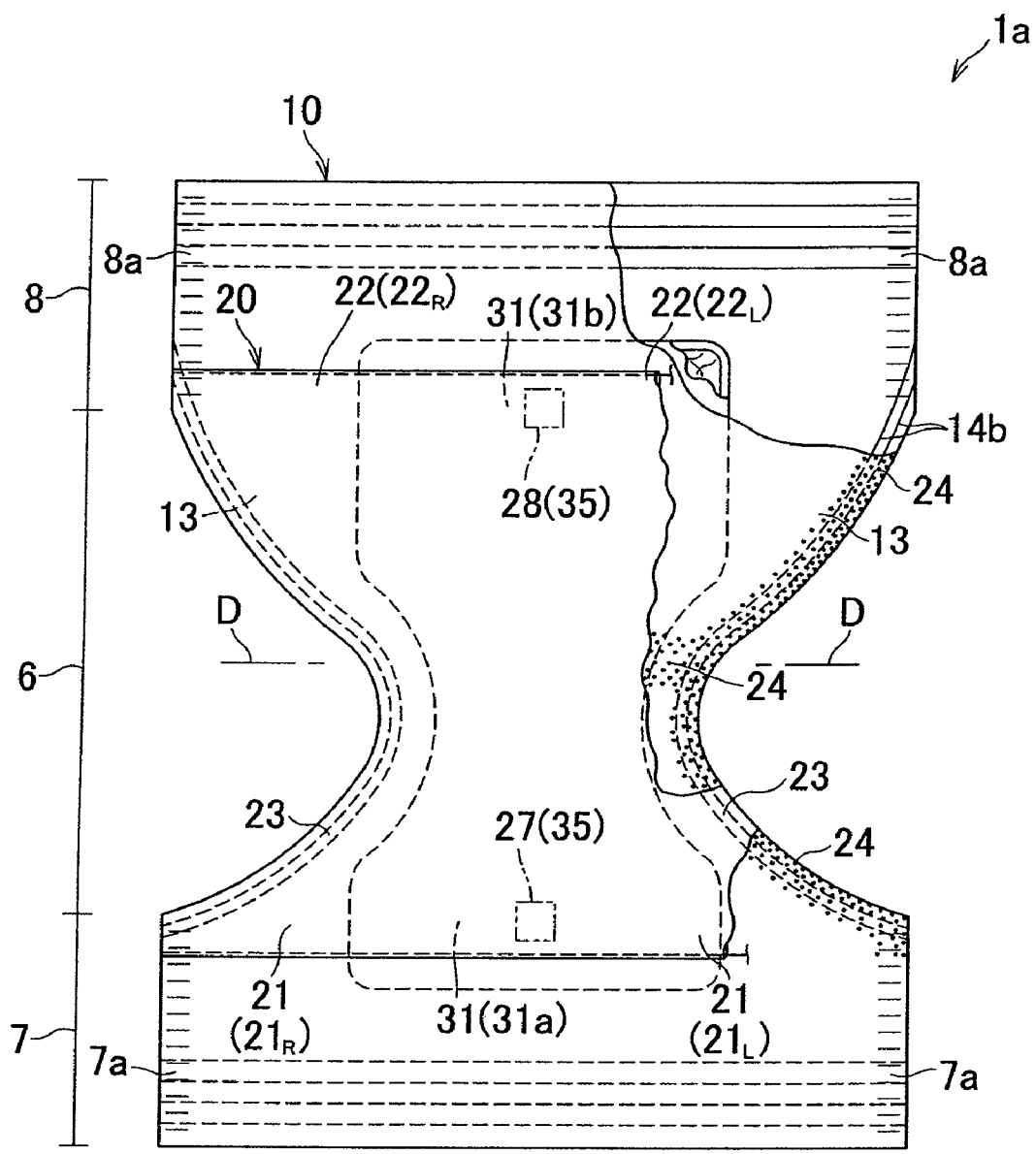
FIG. 5 is a view similar to FIG. 2, showing one preferred embodiment of the invention.

FIG. 5 is a view similar to FIG. 2, showing one preferred embodiment of the invention. In the developed diaper 1a of FIG. 5, the separator 20 has its dimension in the longitudinal direction Y larger than the corresponding dimension of the separator 20 in the developed diaper 1a of FIG. 2. This separator 20 has its front end 21 lying in the front waist region 7 so as to extend between the lateral edges 7a, 7a and the rear end 22 lying in the rear waist region 8 so as to extend between the lateral edges 8a, 8a. This separator 20 has its lateral edges 23 bonded to the lateral edges 13 of the crotch region 6 and to the lateral edges 7a, 8a of the front and rear waist regions 7, 8 in the diaper chassis 10 by hot melt adhesives 24. The separator 20 is also bonded, at its zone extending across the crotch region 6 along the transverse center line D-D, to the inner sheet 2 by hot melt adhesives 24 so that the bodily discharge receiving space 31 formed from the separator 20 and the inner sheet 2 may be divided into a front receiving space 31a and a rear receiving space 31b. By folding back the developed diaper 1a along the transverse center line D-D, joining the front and rear waist regions 7, 8 along the respective lateral edges 7a, 8a and placing the joint zone 27 provided in the vicinity of the front end 2 of the separator 20 and the joint zone 28 provided in the vicinity of the rear end 22 of the separator 20 on each other so as to form the joint 35 (See FIG. 2). In the pull-on type diaper 1 obtained in this manner, the lateral edges 13 including the leg-encircling elastic members 14b define the leg-holes 12 as shown in FIGS. 1 and 3 and can serve as the secondary seals $52_R$, $52_L$ as shown by FIG. 3. The feature that the front and rear end 21, 22 are at the same distance from the transverse center line D-D permits the wearer's right leg to be led through the opening defined between the right front end $21_R$ and the right rear end $22_R$ both extending from the lateral edges 7a, 8a bonded together to the joints 35 in the vicinity of the front and rear ends 21, 22, respectively. Similarly, the left leg can be led through the opening defined between the left front end $21_L$ and the left rear end $22_L$. The right front end $21_R$ and the right rear end $22_R$ are elastically held in close contact with the right leg while the left front end $21_L$ and the left rear end $22_L$ are elastically held in close contact with the left leg. In this way, these front and rear ends function as the primary seals $51_R$, $51_L$ for the right leg and the left leg, respectively. It should be noted here that the primary seals $51_R$, $51_l$ and the secondary seals $52_R$, $52_L$ originated from the developed diaper 1a of FIG. 5 different from those as shown in FIG. 4 in that the primary seals $51_R$, $51_L$ do not intersect with the secondary seals $52_R$, $52_L$. The pull-on type diaper 1 obtained from the developed diaper 1a according to this embodiment also is advantageously free from the problem that urine and feces might be mixed together since the bodily discharge receiving space 31 is partitioned by the separator 20 bonded to the inner sheet 2 into the front half and the rear half.

Figure 6:
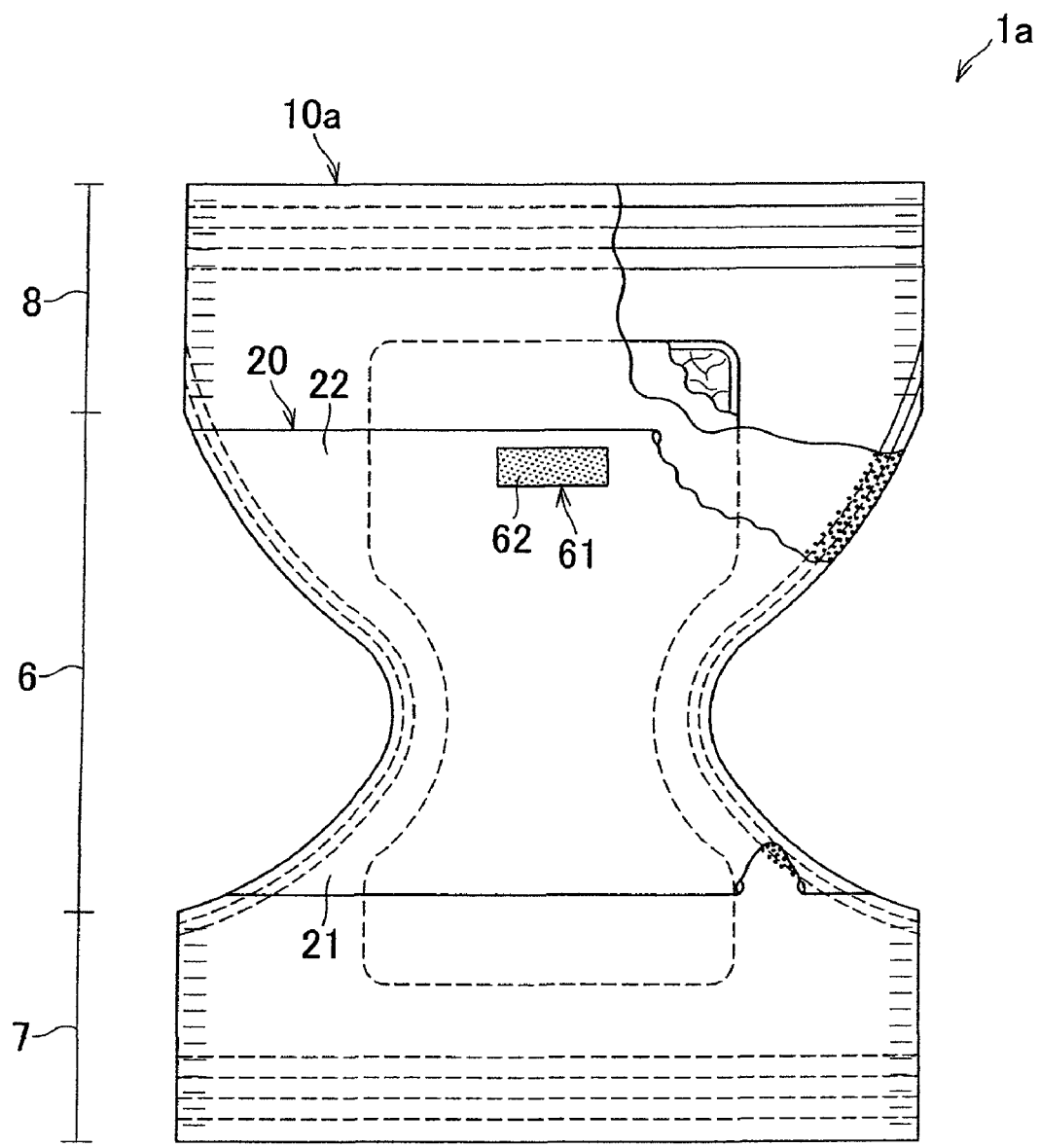
FIG. 6 is a view similar to FIG. 2, showing another preferred embodiment of the invention.
Figure 7:
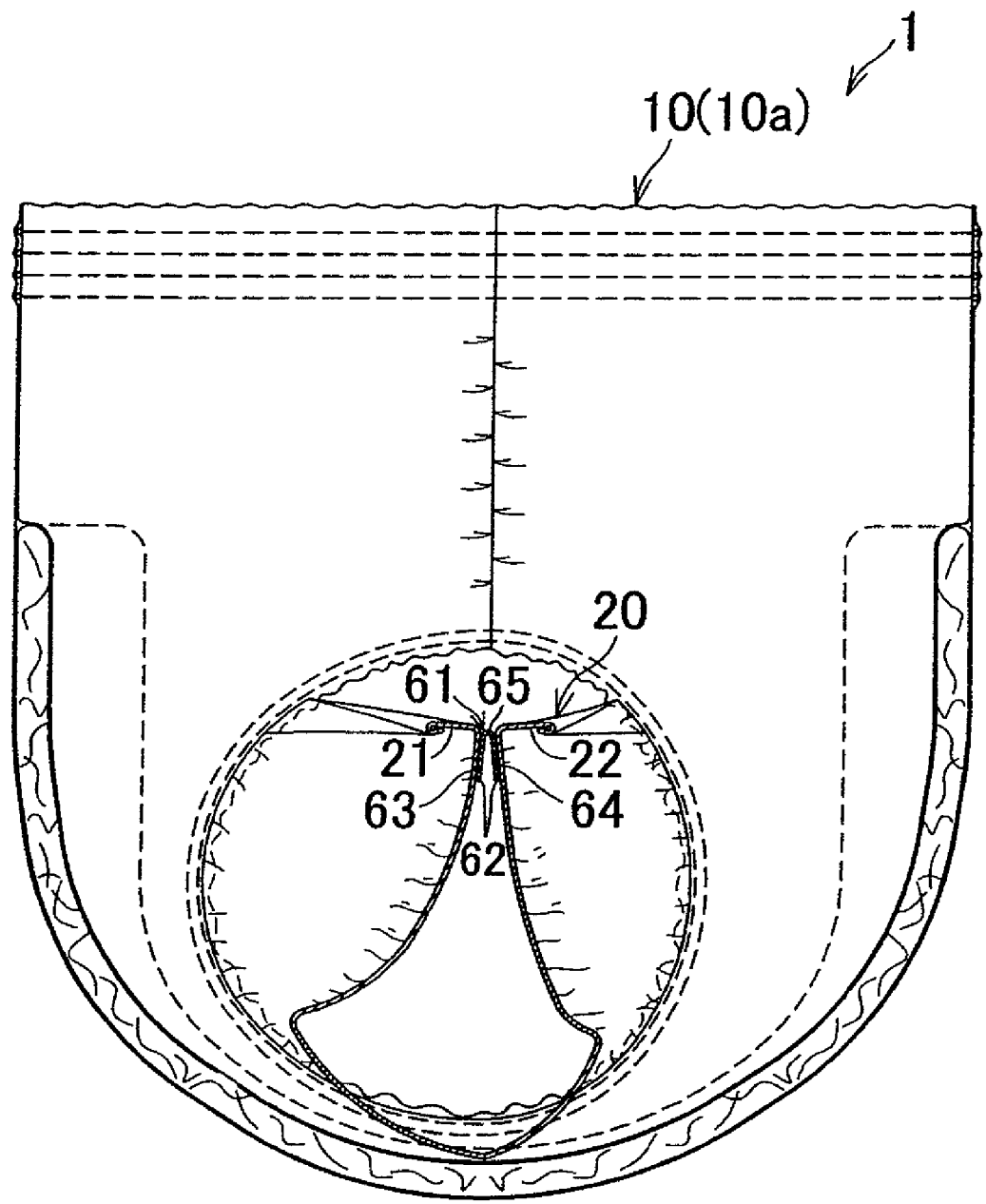
FIG. 7 is a view similar to FIG. 3, showing the embodiment of FIG. 6.

FIG. 6 is a view similar to FIG. 2, showing another preferred embodiment of the invention and FIG. 7 is a view similar to FIG. 3, showing the embodiment of FIG. 6. However, the separator 20 in the developed diaper 1a of FIG. 6 is not provided with the front elastic member 21b and the rear elastic member 22b both used by the developed diaper 1 of FIG. 2. In addition, the developed diaper 1a according to this embodiment is distinguished from the embodiment shown in FIG. 2 in that the front end 21 and the rear end 22 of the separator 20 are adapted to be bonded to each other by means of separately prepared self-adhesive joining member 61. While elastic sheet materials such as elastically stretchable/contractible nonwoven fabrics or plastic films are preferably used for the separator 20 of FIG. 6, it is also possible to use inelastic sheet material for this purpose. The separator 20 formed from the elastic sheet material is not readily creased and therefore there is unlikely that bodily fluids might flow between the wearer's skin and the creased separator 20 in unpredictable direction. The joining member 61 is used in the place of the joint zones 27, 28 adapted to be bonded together by adhesives or the like to obtain the joint 35. The joining member 61 comprises, as seen in FIG. 7, a front portion 63 which is inverted V-shaped in cross-section and adapted to be bonded to the front end 21 by adhesives 62, a rear portion 64 adapted to be bonded to the rear end 22 by means of adhesive 62 and an intermediate portion 65 interposed between these two portions 63, 64.

Figure 8:
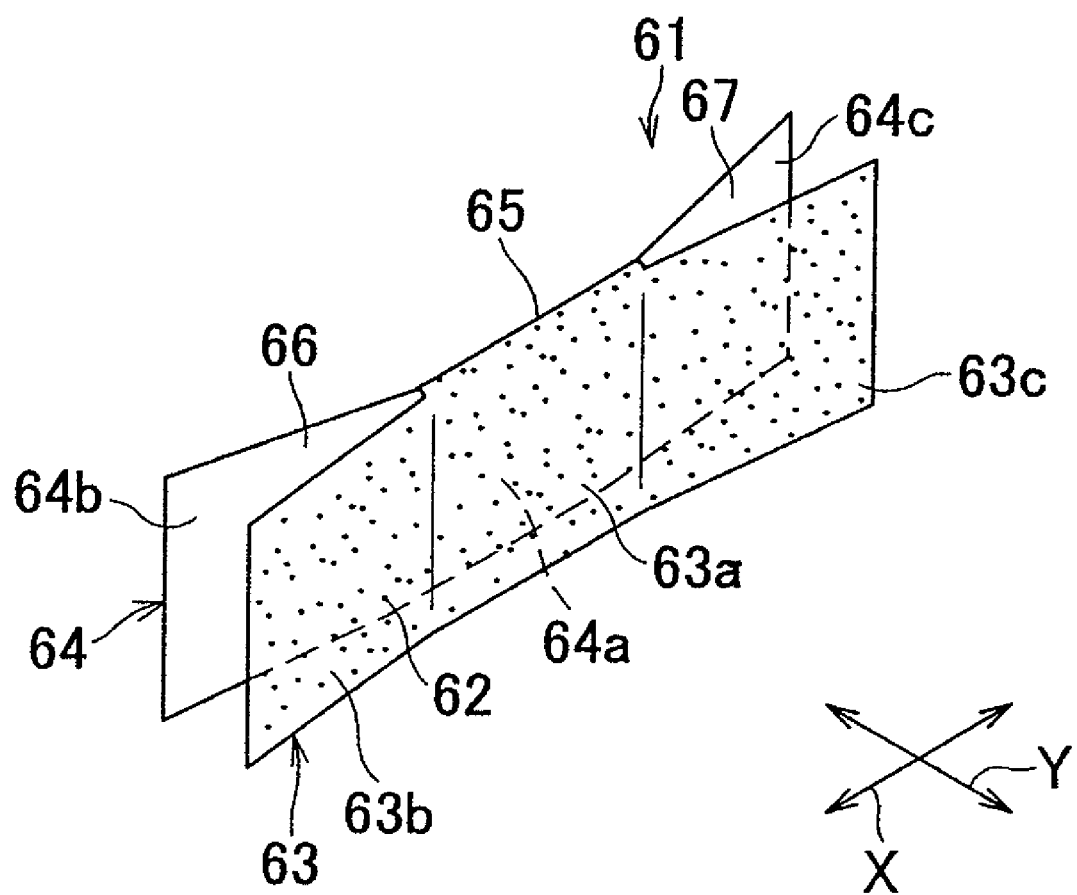
FIG. 8 is a perspective view illustrating a joining member.

FIG. 8 is a perspective view showing a joining member 61. The joining member 61 is made of sheet material such as nonwoven fabric, paper, plastic film folded back along a center line 65 into a front section 63 and a rear section 64. These front and rear sections 63, 64 are coated with joining agent 62 such as adhesive or pressure-sensitive adhesives. The front section 63 and the rear section 64 respectively include intermediate sections 63a, 64a as viewed in a width direction X connected by fold line 65. Opposite end sections 63b; 63c and 64b; 64c as viewed in the width direction X are separated one from another in the back-and-forth direction Y by slits 66, 67. While the dimension of the joining member 61 is not specified, the opposite end sections 63b; 63c and 64b; 64c may be dimensioned to be relatively large in the width direction X to facilitate the developed diaper 1a of FIG. 6 to be folded back on itself and then the front end 21 and thereby to facilitate the rear end 22 of the separator 20 to be joined. Unless a dimension of the intermediate section 65 as viewed in the width direction X is unacceptably enlarged, the front end 21 and the rear end 22 may be integrated with each other by means of the joining member 61 without an anxiety that free movement of these front and rear ends might be constricted. By broadening the widths of the respective slits 66, 67 as viewed in the back-to-forth direction Y, the dimension of the intermediate section 65 as viewed in the back-to-forth direction can be broadened. In other words, by adjusting the dimension of the intermediate section 65 as viewed in the back-to-forth direction Y, the distance between the front end 21 and the rear end 22 of the separator 20 in the pull-on type diaper 1 can be adjusted.

Figure 9:
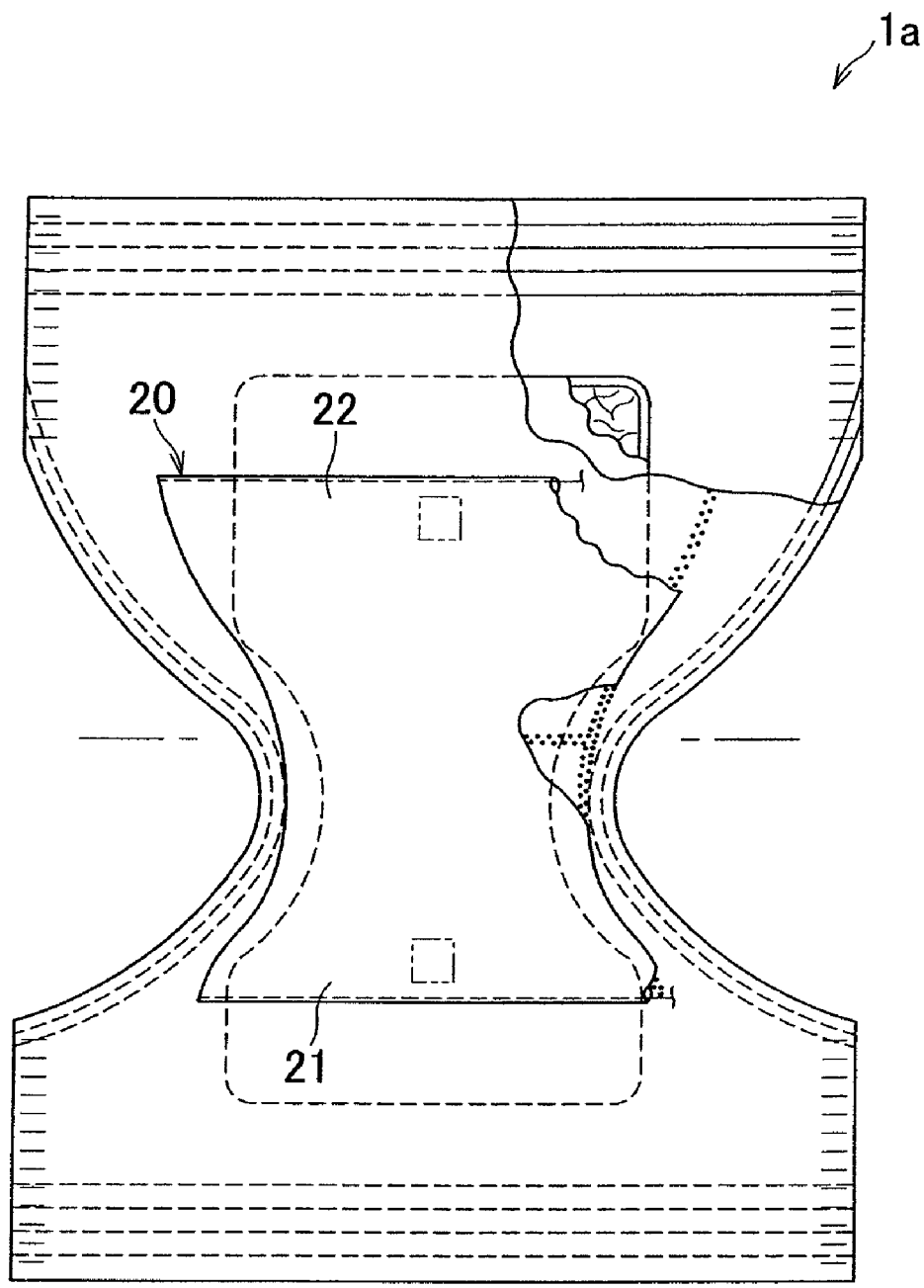
FIG. 9 is a view similar to FIG. 2, showing still another preferred embodiment of the invention.
Figure 9:
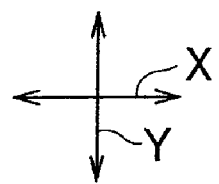

FIG. 9 is a view similar to FIG. 2, showing still another preferred embodiment of the invention. The separator 20 in the developed diaper 1a of FIG. 7 has its dimension in the transverse direction X shorter than in the case of FIG. 2. If it is unnecessary to hold the front end 21 and the rear end 22 of the separator 20 in close contact with the wearer's legs over a wide range, the separator 20 having a relatively small dimension in the transverse direction X can be used.

Figure 10:
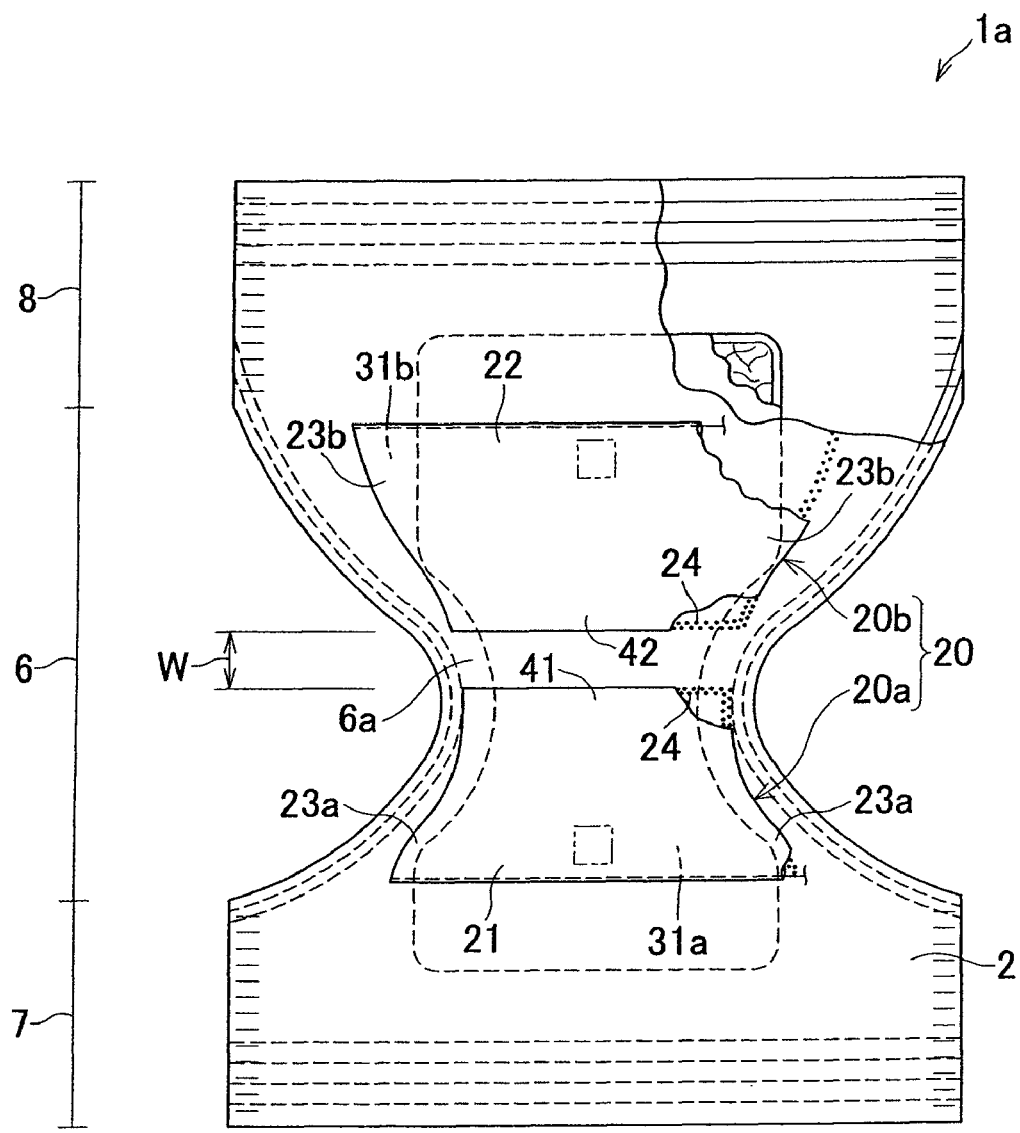
FIG. 10 is a view similar to FIG. 7, showing yet another preferred embodiment of the invention.

FIG. 10 is a view similar to FIG. 7, showing yet another preferred embodiment of the invention. The separator 20 of FIG. 8 is divided into a front separator 20a and a rear separator 20b spaced from each other by a distance W in the longitudinal direction Y. The front separator 20a has the front end 21, a front bottom end 41 lying at the bottom 6a of the crotch region 6 and extending in parallel to the front end 21 in the transverse direction X and lateral edges 23a. The front bottom end 41 and the lateral edges 23a are bonded to the inner sheet 2 by hot melt adhesives 24 and cooperate with the inner sheet 2 to form a front receiving space 31a. The rear separator 20b has the rear end 22, a rear bottom end 42 lying at the bottom and extending in parallel to the rear end 22 in the transverse direction X and lateral edges 23b. The rear bottom end 42 and the lateral edges 23b are bonded to the inner sheet 2 by hot melt adhesives 24. In this developed diaper 1a, the inner sheet 2 is exposed at the bottom 6a by a dimension W in the longitudinal direction Y and consequentially body fluids can be quickly absorbed at the bottom 6a even if body fluids flow along the inner surface of the separator 20 instead of flowing directly into the front receiving space 31a or into the rear receiving space 31b.

Figure 11:
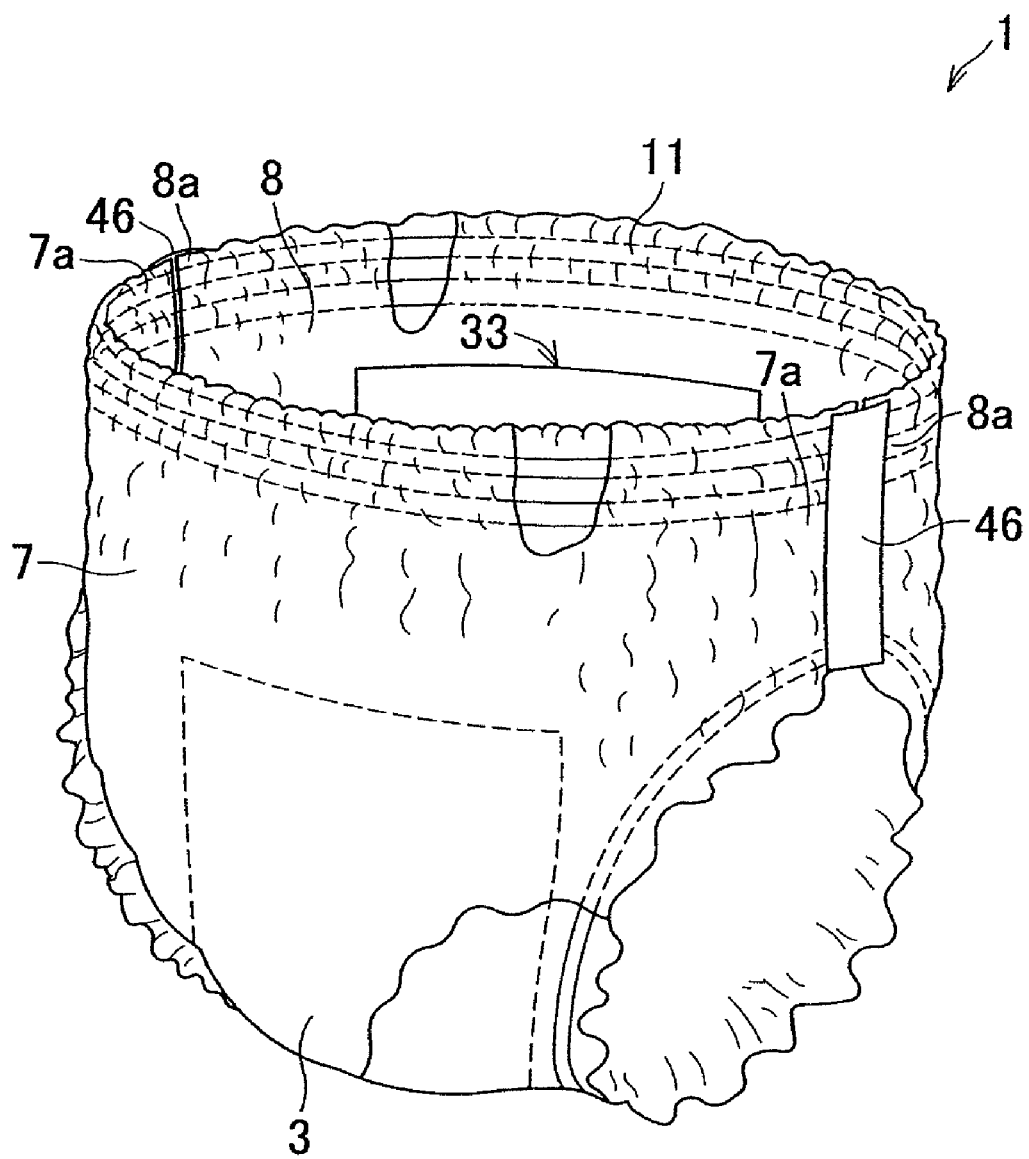
FIG. 11 is a view similar to FIG. 1, showing further another preferred embodiment of the invention.

FIG. 11 is a view similar to FIG. 1, showing further another preferred embodiment of the invention. The pull-on type diaper 1 according to this embodiment is provided along the lateral edges 8a of the rear waist region 8 with fasteners 46, respectively. The fasteners 46 fully extend along the respective lateral edges 8a and fixed to the outer surface of the front waist region 7 in detachable and reattachable manner. When it is desired to put this pull-on type diaper 1 on baby's body, the waist-hole 11 of the diaper 1 previously shaped in the pull-on type is largely broadened and then the sequence for the pull-on type diaper 1 of FIG. 1 is followed. Merely by peeling off the fasteners 46 from the front waist region 7, it is facilitated to check whether bodily discharges are present or not or to take off the diaper 1 contaminated with bodily discharged.

Figure 12:
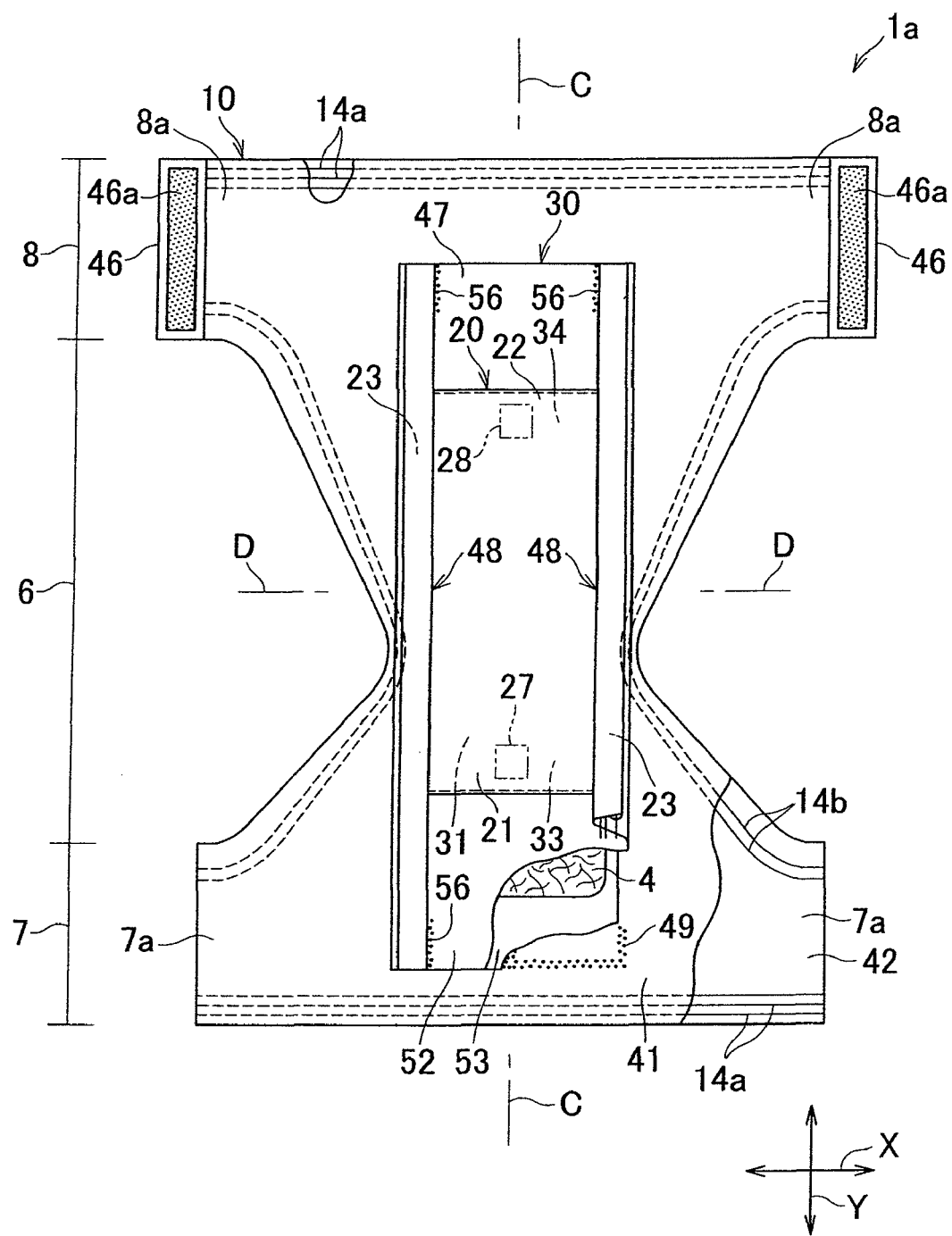
FIG. 12 is a plan view, partially cutaway, showing the pull-on type diaper of FIG. 11.

FIG. 12 is a partially cutaway plan view of the developed diaper 1a. This developed diaper 1a is obtained by detaching the fasteners 46 of the pull-on type diaper 1 of FIG. 9 from the front waist region 7, releasing the joint formed by cooperation of the front joint zone 27 with the rear joint zone 28 (See FIG. 3) and developing the crotch region 6, the front waist region 7 and the rear waist region 8 in the transverse direction X as well as in the longitudinal direction Y. This developed diaper 1a comprises the substantially hourglass-shaped diaper chassis 10 and an absorbent assembly 30 attached to the inner surface of the diaper chassis 10. The absorbent chassis 10 comprises, in addition to the fasteners 46, a first sheet 41 defining the inner surface, a second sheet 42 defining the outer surface, a waist-encircling elastic member 14a and leg-encircling elastic members 14b both attached in stretched state to at least one of these first and second sheets 41, 42. The body fluid absorbent assembly 30 comprises a main frame 47, leak-barriers 48 and the separator 20. The main frame 47 is a substantially rectangular unit extending from the crotch region 6 into the front waist region 7 as well as into the rear waist region 8 and bonded to the absorbent chassis 10 by hot melt adhesives 49. The leak-barriers 48 respectively extend along lateral edges of the body fluid absorbent assembly 30 in the longitudinal direction Y. The separator 20 is provided between the pair of the leak-barriers 48. The separator 20 is symmetric about the longitudinal center line C-C as well as about the transverse center line D-D and has the front joint zone 27 and the rear joint zone 28 on the longitudinal center line C-C.

Figure 13:
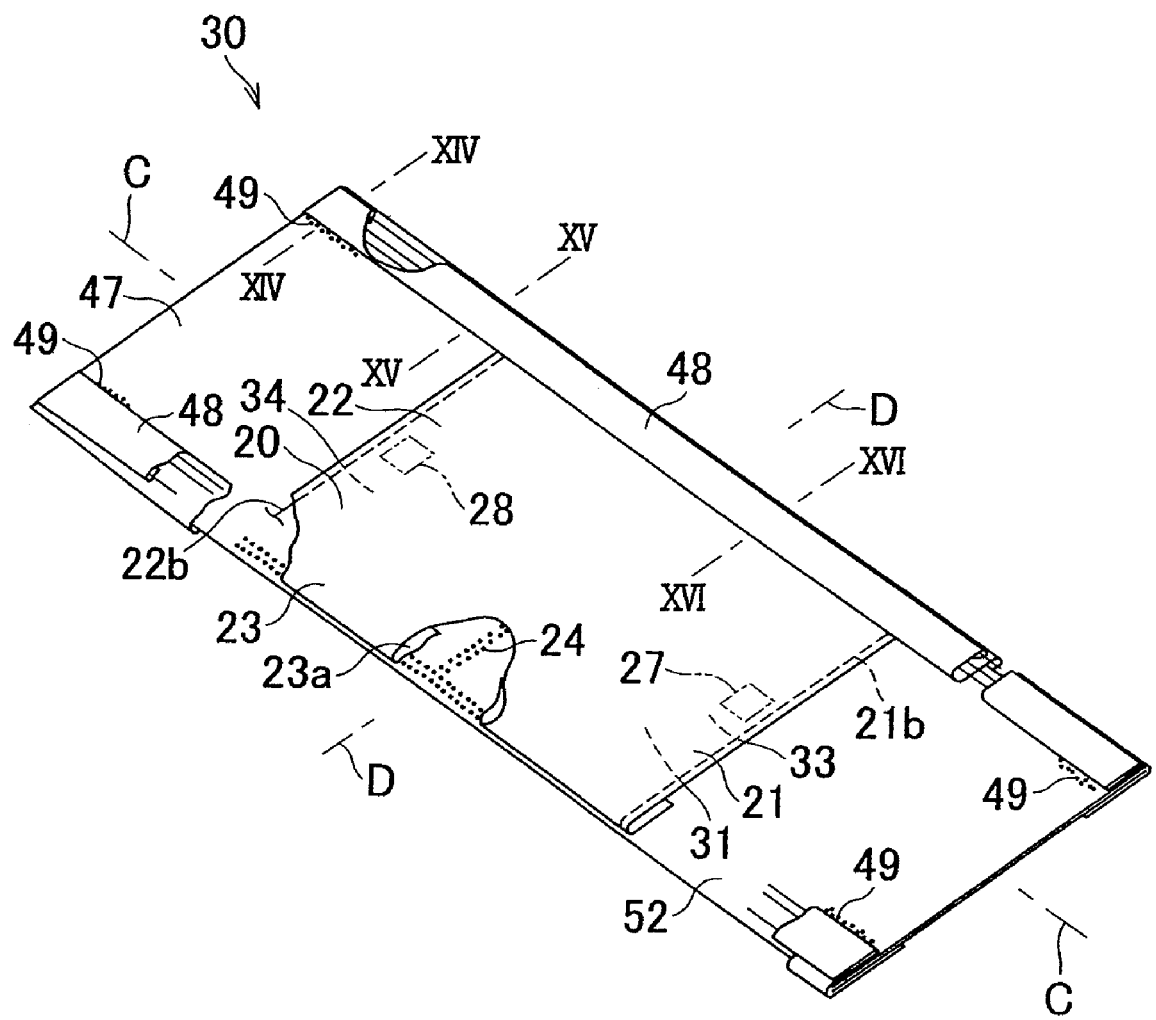
FIG. 13 is a perspective view, partially cutaway, showing a body fluid absorbent core.
Figure 14:
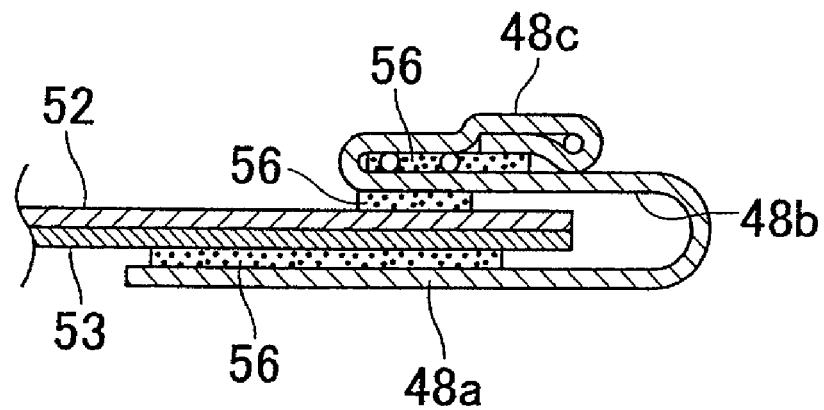
FIG. 14 is a sectional view taken along the line XIV-XIV in FIG. 13.
Figure 15:
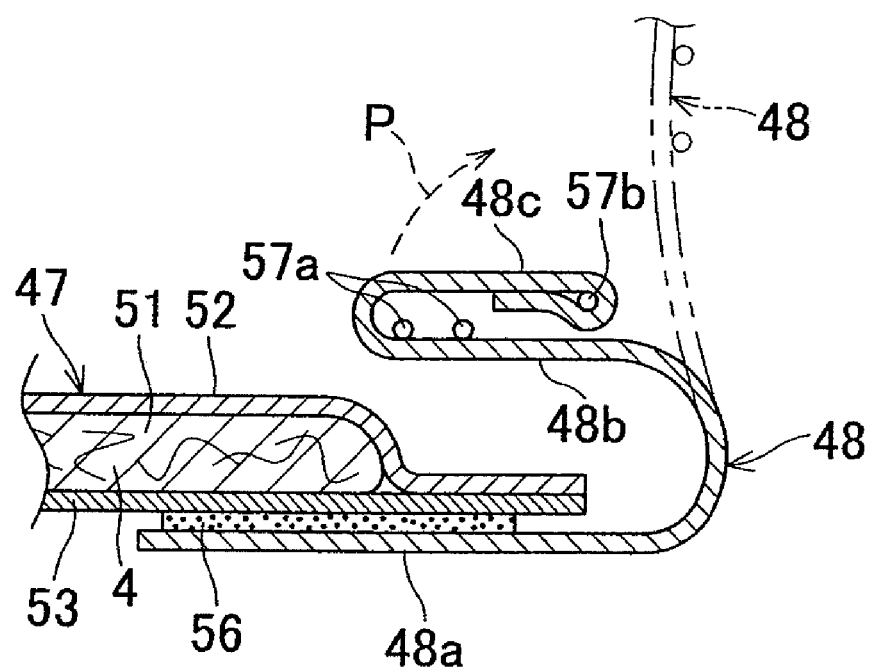
FIG. 15 is a sectional view taken along the line XV-XV in FIG. 13.
Figure 16:
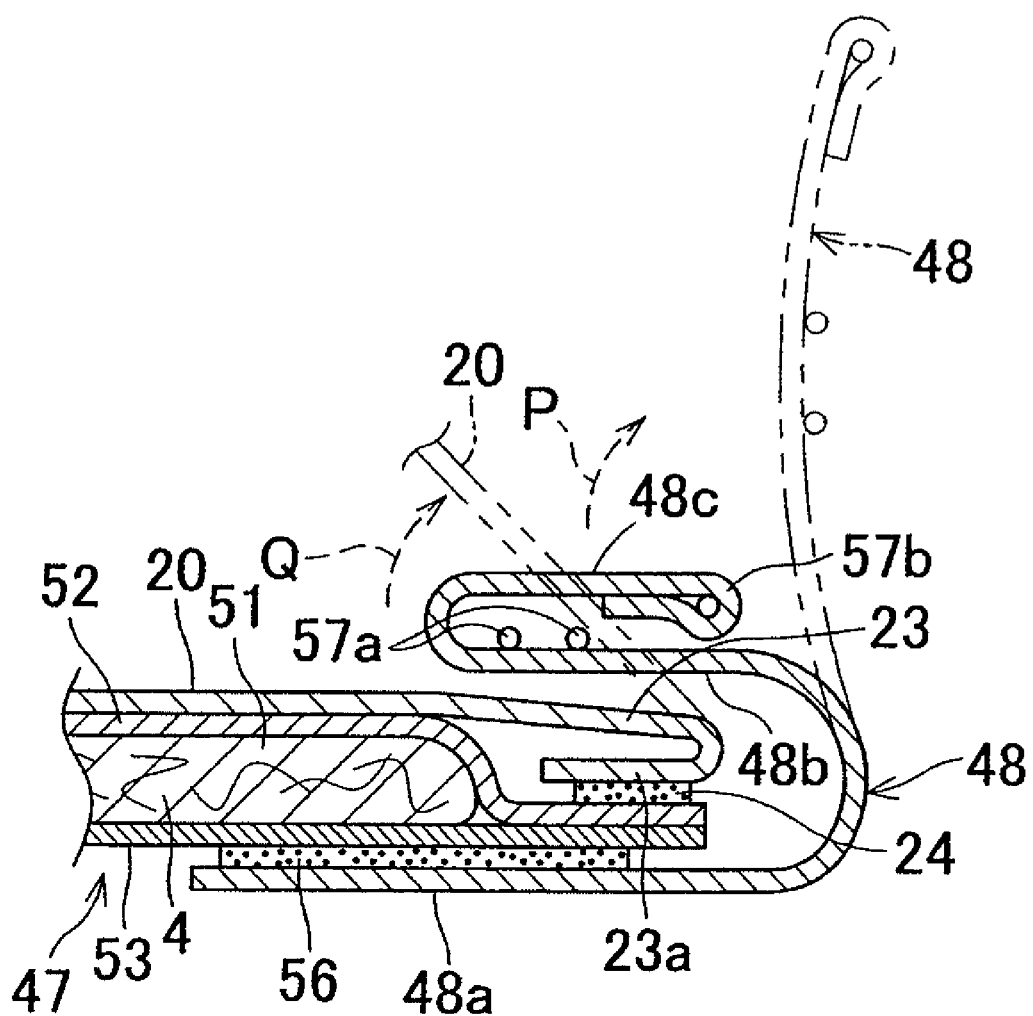
FIG. 16 is a sectional view taken along the line XVI-XVI in FIG. 13.

FIG. 13 is a partially cutaway perspective view showing the body fluid absorbent core 30, FIG. 14 is a sectional view thereof taken along a line XIV-XIV, FIG. 15 is a sectional view taken along a line XV-XV and FIG. 16 is a sectional view taken along a line XVI-XVI. The paired leak-barriers 48 provided along the lateral edges of the absorbent assembly 30 are formed from folding nonwoven fabrics, preferably liquid permeation retardant nonwoven fabrics, more preferably liquid-impervious nonwoven fabrics in a Z- or inverted Z-shape and longitudinally opposite ends of the respective barriers 48 are fixed to the inner surface of the main frame 47 by hot melt adhesives 49. In the main frame 47, as will be apparent from FIGS. 14 through 16, the absorbent core 4 is sandwiched between a liquid-pervious topsheet 52 and a liquid-impervious backsheet 53. The topsheet 52 and the backsheet 53 extend outward beyond a peripheral edge of the core 4 so that, outside the peripheral edge of the core 4, these top- and backsheets 52, 53 are placed upon and bonded to each other by adhesives or appropriate sealing techniques. Each of the leak-barriers 48 folded in the Z- or the inverted Z-shape in this manner comprises a bottom layer 48a, a top layer 48c and an intermediate layer 48b connecting these bottom and top layers 48a, 48c wherein the bottom layer 48a is bonded to the backsheet 53 by hot melt adhesives 56. Referring to FIG. 14, the intermediate layer 48b is bonded to the topsheet 52 by hot melt adhesives 56 and the top layer 48c is bonded to the intermediate layer 48b by hot melt adhesives 56. Referring to FIG. 15, the bottom layer 48a of the leak-barrier 48 is bonded to the backsheet 53 while the intermediate layer 48b and the top layer 48c are folded so that these layers 48b, 48c may rise up in a direction P as indicated by imaginary lines. Referring to FIG. 16, the separator 20 is placed upon the upper surface of the topsheet 52, the lateral edge 23 of the separator 20 is folded back toward the longitudinal center line C-C and the folded portion 23a of this lateral edge 23 is bonded to the topsheet 52 by hot melt adhesives 24. In the leak-barrier 48 of FIG. 16, the bottom layer 48a is bonded to the backsheet 53 while the intermediate layer 48b and the top layer 48c are folded so that these layers 48b, 48c may rise up as indicated by imaginary lines in the same manner as shown in the FIG. 15. The leak-barrier 48 is provided on its intermediate layer 48b with an elastic member 57a attached in a stretched state thereto by hot melt adhesives (not shown) and in the vicinity of a distal end of its top layer 48c with an elastic member 57b bonded in stretched state thereto by hot melt adhesives (not shown). The separator 20 is bonded to the topsheet 52 by hot melt adhesives (24) not only along the lateral edges 23 but also in a zone lying on the transverse center line D-D. The elastic members 21b, 22b are attached in stretched state to the front end 21 and the rear end 22 of the separator 20, respectively. The separator 20 cooperates with the topsheet 52 to form the bodily discharge receiving space 31 having the front opening 33 and the rear opening 34.

For supply to the consumers, the developed diaper 1a of FIG. 12 constructed as has been described above is folded back along the transverse center line D-D so that the front waist region 7 and the rear waist region 8 are placed upon each other with the body fluid absorbent assembly 30 inside, the joint zones 27, 28 are joined together to form the joint 35 (See FIG. 3) and joining zones 46a (See FIG. 12) of the respective fasteners 46 are anchored on the respective lateral edges 7a of the front waist region 7. If plastic film is used as the second sheet 42 defining the outer surface of the front waist region 7, the joining zones 46a of the respective fasteners 46 are preferably formed by pressure-sensitive adhesive and if the second sheet 42 is made of nonwoven fabrics or the like adapted to be engaged with hook members of so-called mechanical fasteners, the joining zones 46a of the respective fasteners 46 are preferably formed by such hook members.

In the pull-on type diaper 1 obtained by placing the front and rear waist regions 7, 8 upon each other and connecting these waist regions 7, 8 with each other by the fasteners 46 starting from the developed diaper 1a of FIG. 12, the separator 20 also is folded back onto itself along the transverse center line D-D. In this pull-on type diaper 1, the front and rear ends 21, 22 of the separator 20 extending in parallel to each other in the transverse center line D-D in FIG. 12 are deformed together so as to describe the V-shape (See FIG. 4) about the joint zones 27, 28 in which these front and rear ends 21, 22 are joined to each other as the front and rear waist regions 7, 8 are drawn apart from each other in the back-to-forth direction and thereby the waist-hole 11 are broadened as seen in FIG. 11. Thereupon, the front opening 33 of the bodily discharge receiving space 31 defined by the front end 21 and the topsheet 52 is also automatically broadened. Furthermore, the lateral edges 23 of the separator 20 move in the direction Q indicated by imaginary lines as will be apparent from FIG. 16 so as to force the intermediate layers 48b and the top layers 28c of the respective leak-barriers 48 upward and thereby to ensure that these layers 48b, 48c rise up as indicated by imaginary lines.

The present invention makes it possible to make a disposable pull-on type diaper free from anxiety that the diaper wearer's skin might be contaminated with feces.

The entire discloses of Japanese Patent Application Nos. 2006-105663 filed on Apr. 6, 2006 and 2006-308358 filed on Nov. 14, 2006, respectively, including specification, drawings and abstract are herein incorporated by reference in their entirety.

What is claimed is:
1. A disposable pull-on type diaper comprising:
a crotch region;
a front waist region extending in a longitudinal direction of the diaper forward from said crotch region; and a rear waist region extending in the longitudinal direction rearward from said crotch region;

wherein said front waist region and said rear waist region are joined together along respective lateral edges thereof so as to define an absorbent chassis;

a separator on an inner surface of the chassis to protect a wearer's skin from contacting with feces discharged by the wearer;

said separator comprising a piece of sheet extending in the longitudinal direction from said crotch region toward said front waist region as well as toward said rear waist region, extending across a longitudinal center line bisecting a width of said crotch region, and being fixed to said inner surface of said absorbent chassis on both sides of said longitudinal center line;

wherein said sheet has
  a front end extending in a transverse direction of the diaper, either across said crotch region in a front zone thereof or across said front waist region; and
  a rear end extending in the transverse direction, either across said crotch region in a rear zone thereof or across said rear waist region and
  wherein
  both said front end and said rear end respectively have middle zones in said transverse direction which are free from direct attachment to said inner surface of said absorbent chassis,
  the front and rear ends of the separator are directly bonded to each other at the respective middle zones thereof on said longitudinal center line.

2. The diaper as defined by claim 1, wherein
said crotch region has lateral edges extending in the longitudinal direction of said diaper,
said lateral edges respectively defining leg-holes and being provided with leg-encircling elastic members attached in a stretched state thereto so as to define leg-encircling elastic zones adapted to be stretchable/contractible in a circumferential direction around each of said leg-holes and
wherein said front end as well as said rear end of said separator extend to said lateral edges and are joined to said inner surface of said diaper chassis in said leg-encircling elastic zones.

3. The diaper as defined by claim 1, wherein
said crotch region has lateral edges extending in the longitudinal direction of said diaper,
said lateral edges respectively defining leg-holes and being provided with leg-encircling elastic members attached in a stretched state thereto so as to define leg-encircling elastic zones adapted to be stretchable/contractible in a circumferential direction around each of said leg-holes and
wherein said front end as well as said rear end of said separator extend to said lateral edges and are joined to said inner surface of said absorbent chassis at points placed inwardly, in the transverse direction, from said leg-encircling elastic zones toward said longitudinal center line.

4. The diaper as defined by claim 1, wherein said front end and said rear end of said separator include a front elastic zone and a rear elastic zone, respectively, both being stretchable/contractible in said transverse direction.

5. The diaper as defined by claim 1, wherein said separator is joined to the inner surface of the chassis in a middle zone of said crotch region along a joining line extending in the transverse direction of said diaper so as to bisect a dimension of the absorbent chassis in the longitudinal direction of said diaper.

6. The diaper as defined by claim 1, wherein said piece of sheet forming said separator comprises:
  a front piece of sheet lying in said crotch region toward said front waist region; and
  a separated rear piece of sheet lying in said crotch region toward said rear waist region so that said front piece of sheet has said front end and said rear piece of sheet has said rear end.

7. The diaper as defined by claim 6, wherein
said front piece of sheet comprises a front bottom end extending in parallel to said front end in a middle zone of said crotch region; and
said rear piece of sheet has a rear bottom end extending in parallel to said rear end in the middle zone of said crotch region;
wherein said front bottom end as well as said rear bottom end are joined to the inner surface of the chassis of said crotch region along joining lines extending in the transverse direction.

8. The diaper as defined by claim 1, wherein said crotch region comprises, in a middle zone in said transverse direction,
said lateral edges respectively defining leg-holes and being provided with leg-encircling elastic members attached in a stretched state thereto so as to define leg-encircling elastic zones being stretchable/contractible in a circumferential direction around each of said leg-holes; and
a body fluid absorbent core containing at least one of fluff pulp and super-absorbent polymer particles and, on both sides of said absorbent core, flaps each containing at least one of a nonwoven fabric and a plastic film and having a flexural stiffness lower than that of said absorbent core and wherein said leg-encircling elastic zones are formed in said flaps, respectively.

9. The diaper as defined by claim 1, wherein said front waist region and said rear waist region are joined together in detachable and reattachable manner so that said front and rear waist regions may be releasably joined together to define a pull-on type garment before the diaper is put on the wearer's body.

10. The diaper as defined by claim 1, wherein the piece of sheet is hydrophobic.

11. The diaper as defined by claim 1, wherein the front end and the rear end of the separator have a shorter dimension in the transverse direction than that said crotch region.

12. The diaper as defined by claim 1, further comprising an absorbent core which comprises paired barriers extending in the longitudinal direction thereof, wherein said barriers are folded in a Z-shape or inverted Z-shape and fixed to a top surface of the absorbent core by adhesive; and each of said barriers further comprising:
  a top layer;
  a bottom layer bonded to a bottom surface of the absorbent core; and
  a intermediate layer connecting the top layer and the bottom layer and bonded to the top surface of the absorbent core.

13. The diaper as defined by claim 12, wherein each said barrier rises up outwardly of the absorbent core and further comprises at least an elastic member bonded in stretched state thereto by said adhesive.

14. The diaper as defined by claim 13, wherein said separator is attached upon the top surface of the absorbent core and lateral edges of the separator are folded back and bonded to the top surface of the absorbent core.

15. The diaper as defined by claim 1, wherein said separator further comprises lateral edges bonded to the lateral edges of the front and rear waist regions and to lateral edges of the crotch regions,
   wherein said separator is further bonded, along a bonding line extending across the crotch region in a transverse center line of the crotch region, to the inner surface so as to provide a front receiving space and a rear receiving space for the feces discharged by the wearer.

16. The diaper as defined by claim 1, wherein the middle zones are joined together along a length of 3 to 50 mm in the transverse direction.

17. A disposable pull-on type diaper comprising:
   a crotch region;
   a front waist region extending in a longitudinal direction of the diaper forward from said crotch region; and
   a rear waist region extending in the longitudinal direction rearward from said crotch region;
   wherein said front waist region and said rear waist region are joined together along respective lateral edges thereof so as to define an absorbent chassis;
   a separator on an inner surface of the chassis to protect a wearer's skin from contacting with feces discharged by the wearer;
   said separator comprising a piece of sheet extending in the longitudinal direction from said crotch region toward said front waist region as well as toward said rear waist region, extending across a longitudinal center line bisecting a width of said crotch region, and being fixed to said inner surface of said absorbent chassis on both sides of said longitudinal center line;
   wherein said sheet has
      a front end extending in a transverse direction of the diaper, either across said crotch region in a front zone thereof or across said front waist region; and
      a rear end extending in the transverse direction, either across said crotch region in a rear zone thereof or across said rear waist region and
   wherein
   both said front end and said rear end respectively have middle zones in said transverse direction which are free from direct attachment to said inner surface of said absorbent chassis,
   the front and rear ends of the separator are joined to each other at the respective middle zones thereof on said longitudinal center line, and
   the front and rear ends are permanently bonded to each other at the respective middle zones.

* * * * *